(12) United States Patent
Grunden et al.

(10) Patent No.: US 10,555,585 B2
(45) Date of Patent: Feb. 11, 2020

(54) FASTENER

(71) Applicant: BSN medical GmbH, Hamburg (DE)

(72) Inventors: Jennifer Grunden, Hamburg (DE);
Timo Schmeltzpfenning, Buchholz (DE); Joachim Bauer, Hamburg (DE)

(73) Assignee: BSN MEDICAL GmbH, Hamburg (DE)

( * ) Notice: Subject to any disclaimer, the term of this patent is extended or adjusted under 35 U.S.C. 154(b) by 1027 days.

(21) Appl. No.: 14/783,189

(22) PCT Filed: Apr. 17, 2014

(86) PCT No.: PCT/EP2014/057930
§ 371 (c)(1),
(2) Date: Jan. 11, 2016

(87) PCT Pub. No.: WO2014/170446
PCT Pub. Date: Oct. 23, 2014

(65) Prior Publication Data
US 2016/0198809 A1    Jul. 14, 2016

(30) Foreign Application Priority Data
Apr. 17, 2013    (EP) .................................... 13164211

(51) Int. Cl.
*A44B 11/25* (2006.01)
*A44B 11/28* (2006.01)

(52) U.S. Cl.
CPC ................... *A44B 11/28* (2013.01)

(58) Field of Classification Search
CPC ....... A41F 1/00; A44B 11/2584; A44B 11/28; A44B 13/00; Y10T 24/45995; A61F 5/01; A61F 5/373; A61F 5/3738
See application file for complete search history.

(56) References Cited

U.S. PATENT DOCUMENTS

| | | | |
|---|---|---|---|
| 868,298 A | 10/1907 | Siner | |
| 1,188,709 A | 6/1916 | Wenzel | |
| (Continued) | | | |

FOREIGN PATENT DOCUMENTS

| | | |
|---|---|---|
| AT | 338 723 B | 9/1977 |
| DE | 197 45 705 C1 | 2/1999 |
| DE | 11 2011 100 230 T5 | 10/2012 |

OTHER PUBLICATIONS

European Search Report for EP13164211 dated Jul. 10, 2013.

*Primary Examiner* — Jack W Lavinder
(74) *Attorney, Agent, or Firm* — Shumaker, Loop & Kendrick LLP

(57) ABSTRACT

A closure is shown and described, preferably for an orthosis, which has a belt assembly, having a first closure part (1) and a second closure part (21), which can be releasably connected to one another, wherein the first and the second closure parts (1, 21) have connecting means for belts of the belt assembly, wherein the first closure part (1) has a pin (3), wherein the second closure part (21) has a connection end (23) and a coupling end (25), and between the connection end (23) and the coupling end (25) a guide track (37) extending in a closure plane is provided, which extends from an entrance opening (41) to a guide track end (43), wherein the pin (3) has a first section (7) and a second section (9), wherein the dimensions of the first section (7) perpendicular to the direction of extension of the pin (3) correspond to the dimensions of the guide track (37) in the closure plane at the guide track end (43), and wherein the dimensions of the second section (9) perpendicular to the direction of extension of the pin (3) are greater than the dimensions of the guide track (37) at the guide track end (43), so that the second section (9) restricts a movement of the pin (3) relative to the second closure part (21) perpendicular to the closure plane.

12 Claims, 7 Drawing Sheets

(56) References Cited

U.S. PATENT DOCUMENTS

Figure 1:
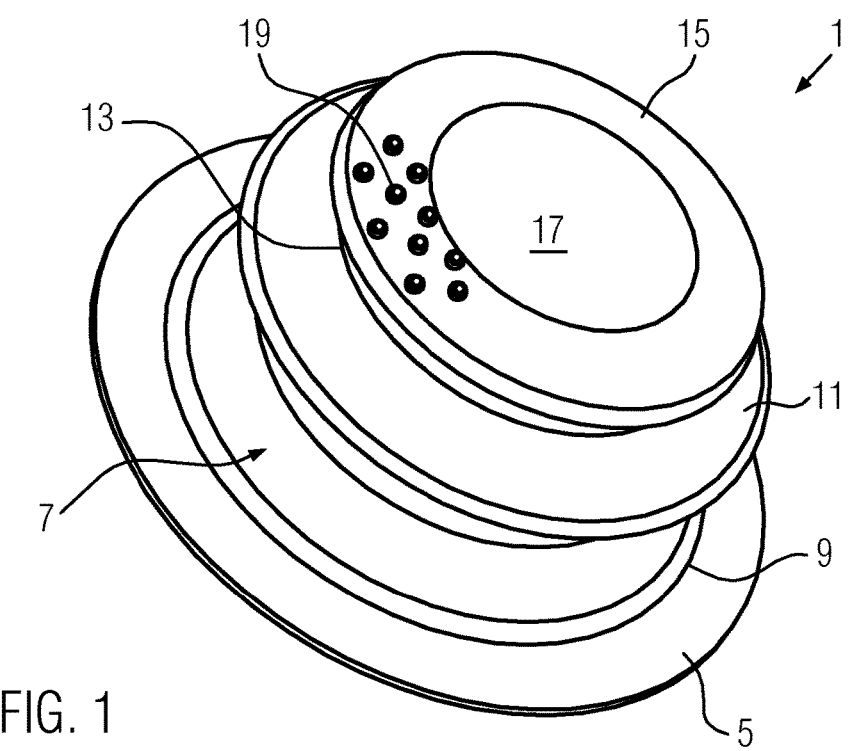

| | | | |
|---|---|---|---|
| 1,428,358 A * | 9/1922 | Burbery | A44B 11/2584 24/702 |
| 6,687,963 B1 | 2/2004 | Chang | |
| 2003/0176823 A1 | 9/2003 | Mason | |
| 2005/0187504 A1 | 8/2005 | Modglin | |

* cited by examiner

FASTENER

The present invention relates to a closure, preferably for an orthosis, having a belt assembly.

Orthoses for immobilization or securing of a joint or for bracing a body part often include a belt assembly, which is appropriately fitted onto the body of the patient in order to secure the joint in question in a predetermined position, for example. It is often necessary for force to be applied to the body via the belt assembly, meaning that the belt assembly must be subjected to a certain preload in the closed state of the orthosis.

On the other hand, it is however often the case that, when an orthosis is already partially fitted on, the patient is severely limited in his/her freedom of movement, and he/she thus finds it difficult to properly connect the belts of the orthosis to one another.

Thus, for example, in the case of the orthosis described in DE 197 45 705 C1, which serves to secure a shoulder joint, it is necessary for the patient to fasten a large number of belt ends with corresponding Velcro closures at predetermined points of the belt assembly. There are significant difficulties associated with this task for the patient who is, on the one hand, limited in his/her freedom of movement by the orthosis that has been fitted on and who, on the other hand, is often additionally impaired as a result of an injury.

A further problem is that the belt assembly of such an orthosis must be subjected to a certain preload, so that the shoulder joint in question is reliably secured in the fitted on position of the orthosis.

Based on the prior art, it is therefore the objective of the present invention to provide a closure for an orthosis having a belt assembly, which allows a patient wearing the orthosis to easily close the belt assembly on the one hand and, on the other hand, which closure ensures that the closing generates the necessary preload inside the belt assembly.

This objective is achieved according to the invention with a closure having a first closure part and a second closure part, which can be releasably connected to one another, wherein the first and the second closure parts have connecting means for belts of the belt assembly, wherein the first closure part has a pin, wherein the second closure part has a connection end, on which the connecting means is formed, and has a coupling end, and between the connection end and the coupling end a guide track extending in a closure plane is provided, which extends from an entrance opening to a guide track end, and which is designed to receive the pin and guide it between the entrance opening and the guide track end along the guide track, wherein the pin has a first section near the connecting means of the first closure part and a second section adjoining the first section and disposed on the end of the first section opposite the connecting means, wherein the dimensions of the first section perpendicular to the direction of extension of the pin correspond to the dimensions of the guide track in the closure plane at the guide track end, and wherein the dimensions of the second section perpendicular to the direction of extension of the pin are greater than the dimensions of the guide track at the guide track end, so that the second section restricts a movement of the pin relative to the second closure part perpendicular to the closure plane, when the pin is at the guide track end.

A closure designed in such a way can be easily closed by the patient, even in the case of a fitted on orthosis having a belt assembly, as the patient must simply insert the pin in the region of the entrance opening into the guide track, and the pin, once it has been moved along the guide track to the guide track end, is then prevented from being released from the guide track, in other words, the two ends of the belt assembly to be connected are interlocked. Because the dimensions of the second section of the pin perpendicular to its direction of extension are greater than the dimensions of the guide track at the guide track end, a movement of the pin perpendicular to the plane of the guide track is prevented, irrespective of the position of the pin relative to the guide track end.

In a preferred embodiment, the guide track is designed such that any possible movement of the pin outside of its position in the guide track end either runs perpendicular to a connecting line between the connection end and the coupling end or the projection of this movement is directed on the connecting line toward the connection end. This design ensures that, under a tension which a belt assembly applies to an orthosis at the closure, the pin is held at the guide track end.

If a closure designed in this way is thus used in an orthosis which is subjected, in the closed state, to a certain preload, resulting in a force being applied to the closure, which runs along the connecting line between the connection end and the coupling end, the following advantage is achieved. When closing the orthosis, the pin only needs to be inserted into the correspondingly dimensioned entrance opening of the guide track and moved along the guide track to the guide track end, with this movement being determined simply by the shape of the guide track and being facilitated by the previously described force.

Because, when the pin is spaced from the guide track end, this force acts on the first closure part, which force pulls the pin to the guide track end. Conversely, the pin must be moved away from the guide track end, counteracting this force, when the orthosis is to be opened. This is also the case when the movement out of the guide track end runs perpendicular to the connecting line, since at least frictional force is then applied, which must be overcome during a movement out of the guide track end. Thus the closure according to the invention locks itself under a preload in the belt assembly.

In another preferred embodiment, the guide track end and the pin are designed such that the first closure part can be pivoted relative to the second closure part, when the pin is located at the guide track end. This makes it possible for the two parts of the closure to align with one another in accordance with the forces acting on them. Here it is possible, in particular, for the first section to have a circular cross-section and for the diameter of the first section to correspond to the width of the guide track end, and preferably of the entire guide track. In this context, the term width is to be understood as the dimension of the guide track perpendicular to its course or perpendicular to respective tangents.

If the width of the entire guide track, if applicable with the exception of a section having a latching projection, corresponds to the diameter of the pin, the pin is guided over the entire length of the guide track, however, it can be pivoted and thus aligned to the acting forces.

It is also advantageous if locking means are provided, in order to hold the pin in the guide track, preferably at the guide track end. In particular, the locking means can be designed such that a latching projection is formed in the guide track, so that the width of the guide track is reduced in the region of the latching projection, with the second closure part being designed such that the first section of the pin, when moving from the entrance opening to the guide track end and back again, must be moved past the latching projection, against an elastic counterforce.

This prevents the pin from being able to move out of the guide track or even away from the guide track end to the entrance opening, without there being any need to apply a force either to the pin itself or to a part of the second closure part. The pin is thus also mechanically locked in its position at the guide track end.

The second closure part preferably has another connecting means for another belt. This means that several belts of the belt assembly of the orthosis can intersect at the second connecting part.

It is also preferred if an abutment section with uniform thickness is provided adjacent to the guide track and in the region of the guide track end, preferably adjacent to the entire guide track, with the first section of the pin having, in its axial direction, a length corresponding to the thickness of the abutment section. In this case, the second closure part is guided between the projections on the pin, and the movement of the pin along the guide track runs only in the plane of the flat section. This permits a simple closure movement, which can be easily implemented, even by a patient who has limited movement.

Furthermore, the guide track can extend to the edge of the second closure part, with the entrance opening being formed in the edge of the second closure part. The first closure part can then be connected to the second in such a way that the closure movement occurs only in the plane of the second closure part, in other words, the second closure part is thus pulled over the pin in the manner of a hook.

It is preferred that the entrance opening is provided between the connection end and the coupling end on a first side of the connecting line between the connection end, with the other connecting means being provided on a second side of the connecting line opposite the first side. In this way, the two closure parts can be engaged with one another by means of a movement in the plane of the flat section, without a belt attached to the other connecting means being in the way.

In such a design it is also preferred that the projection of the entrance opening onto the connecting line between the connection end and the coupling end is further distanced from the coupling end than the projection of the guide track end onto the connecting line. This ensures that the pin is pulled to the guide track end as a result of the preload in the belt assembly, and thus away from the entrance opening.

The guide track preferably extends with a uniform direction of curvature from the entrance opening to the guide track end, which permits simple closing of the closure. If the guide track is designed at the guide track end such that the movement of the pin out of the position on the guide track end runs parallel to the connecting line between the connection end and the coupling end, this ensures that, as a result of the preload, the pin remains reliably at the guide track end.

Finally, in a preferred embodiment, the pin of the first closure part can be designed such that it has a free end, which is provided with a recess extending in the axial direction of the pin. This makes it possible for the patient to fix the pin in its position or move it by placing one finger in the recess, while with the same hand guiding the second closure part to the pin. It is therefore possible to close the closure with one hand.

In addition, the closure can be used in an orthosis having a belt assembly, with the connecting means being connected to ends of the belts of the belt assembly.

In a preferred embodiment, the orthosis is then designed such that it has a circular belt assembly, which is designed to pass around a patient in a circular and horizontal manner, and which has a first and a second section, which are designed to be detachably connected at a point of intersection, having a shoulder belt assembly, which has a first end connected to the circular belt assembly and a second end, and which is adapted so as to run from the back to the front over a shoulder of the patient to the point of intersection, with the first section of the circular belt assembly being connected to the connecting means of the first closure part, with the second section of the circular belt assembly being connected to the connecting means of the second closure part, and with the shoulder belt assembly being connected to the other connecting means of the second closure part.

With such a design, the connecting means according to the invention makes it possible to generate, by means of a single closing movement, a force in the circular belt assembly and a force in the shoulder belt assembly, without this involving a complicated manipulation. In fact, the patient is even able to achieve this without external assistance.

Figure 2:
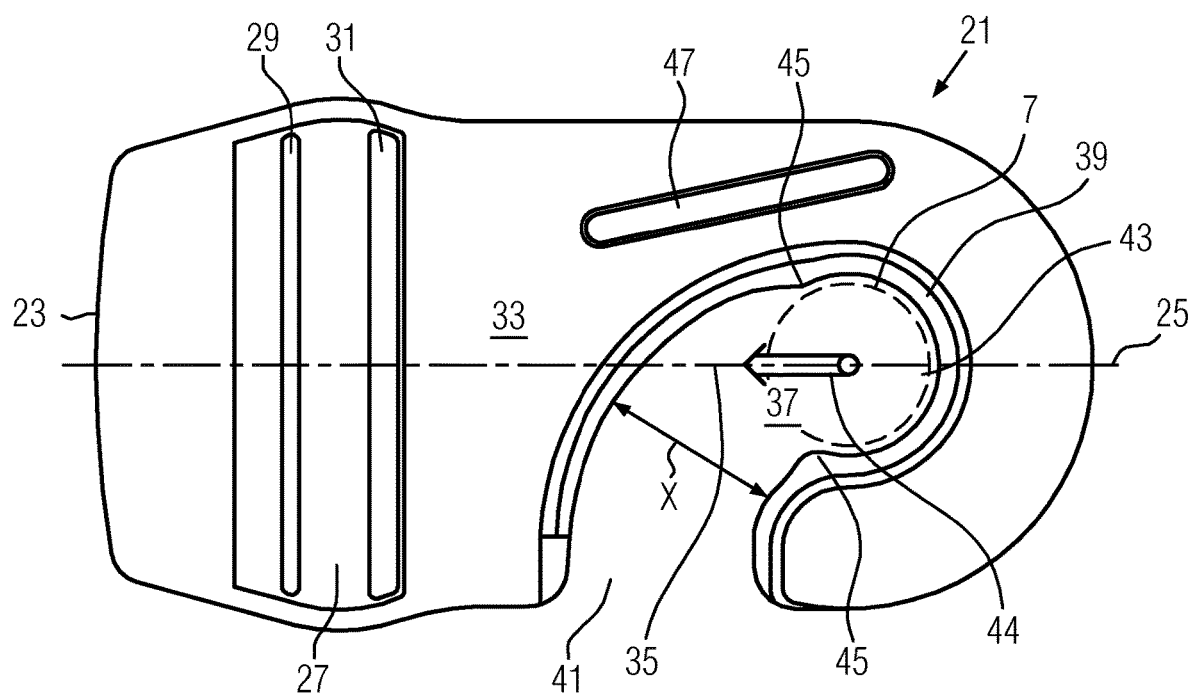
Figure 3:
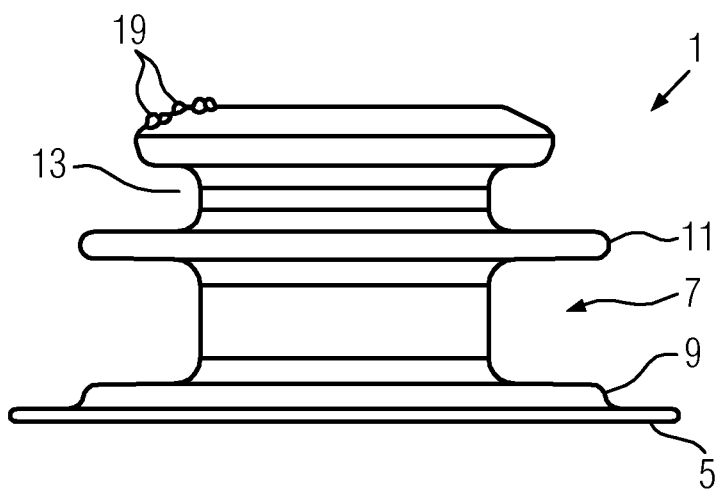
Figure 4:
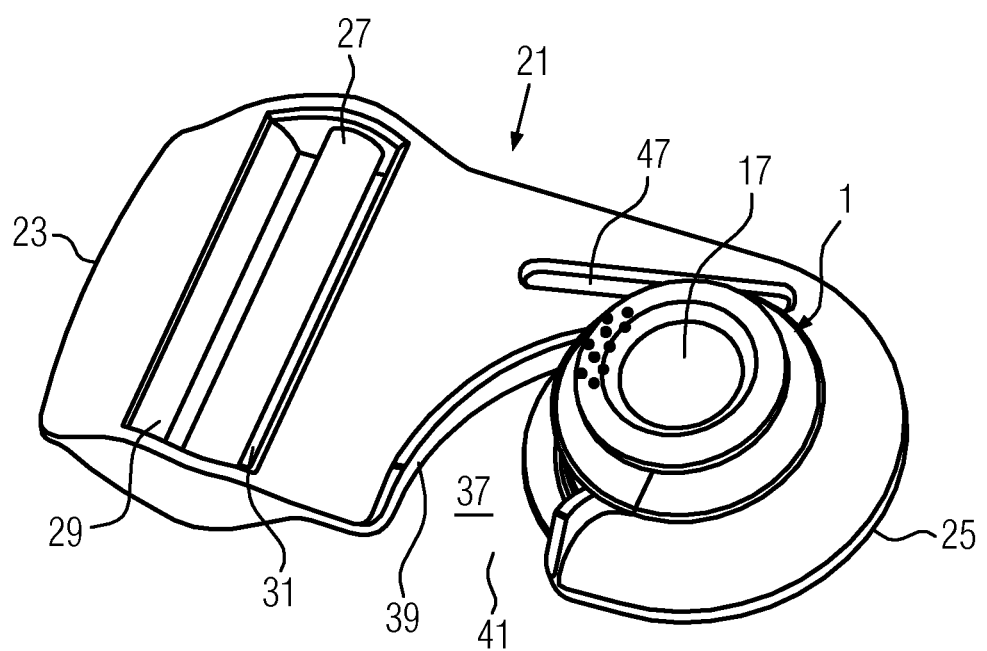
Figure 5:
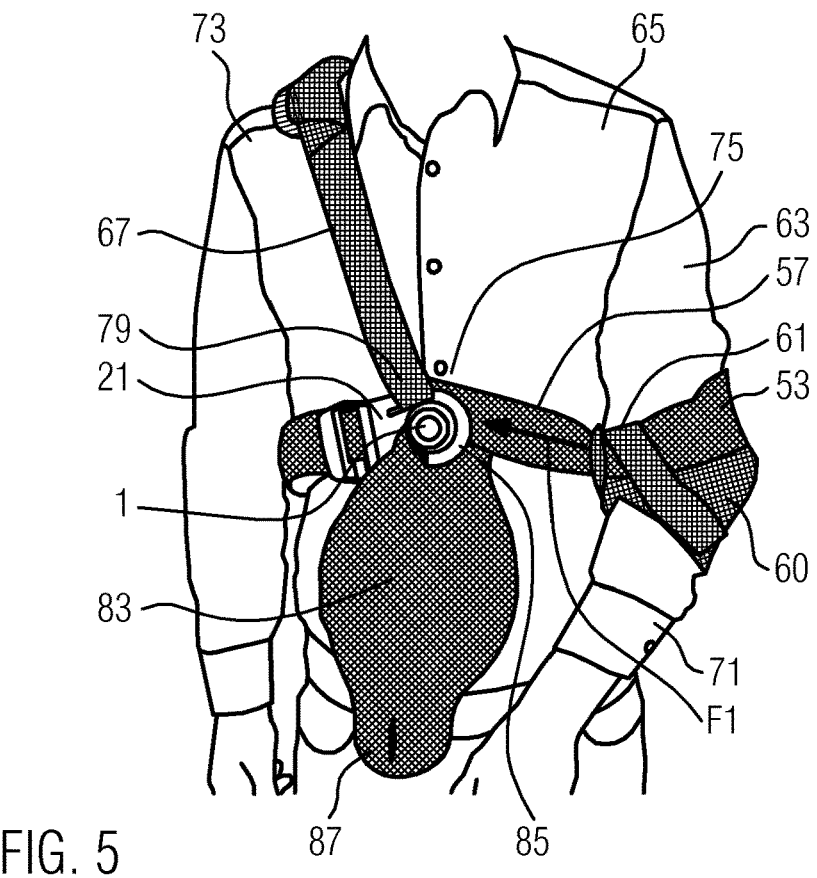
Figure 6:
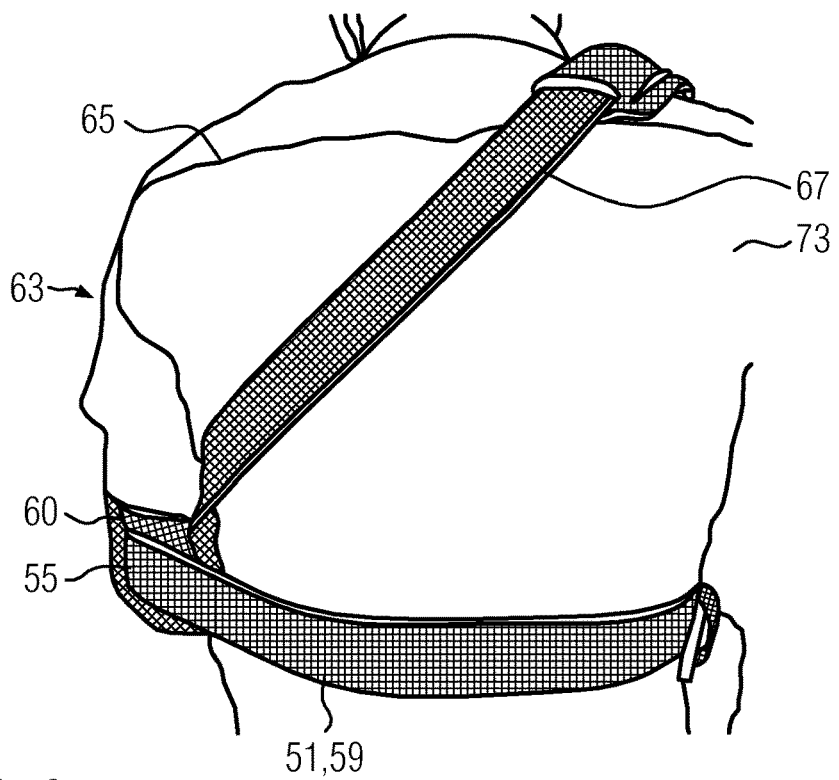
Figure 7:
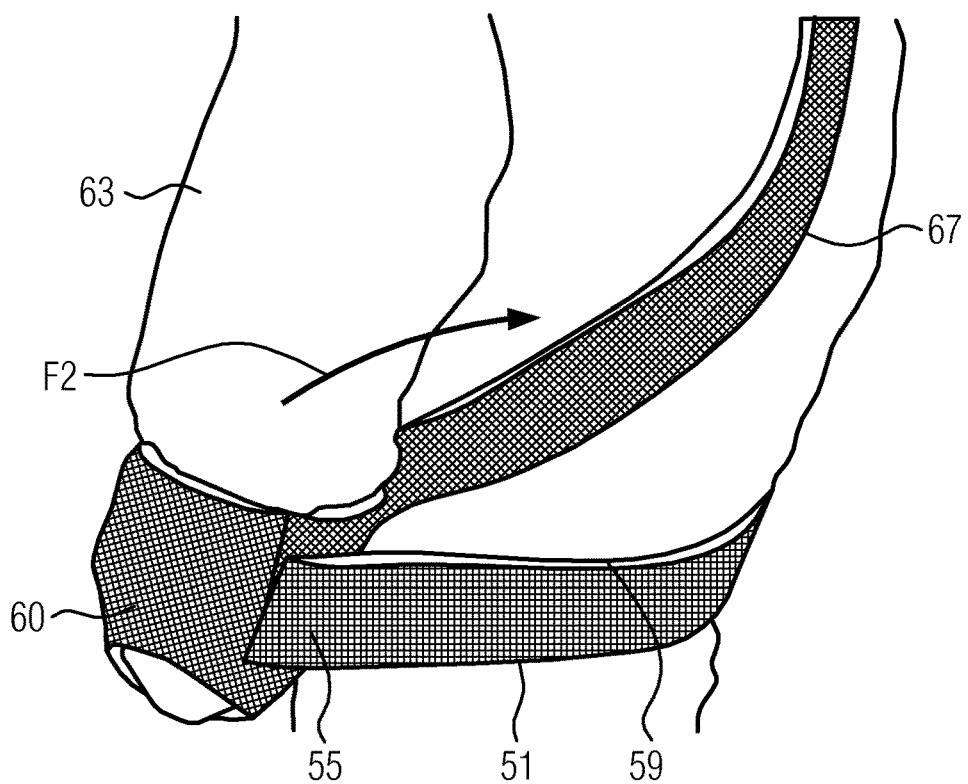
Figure 8:
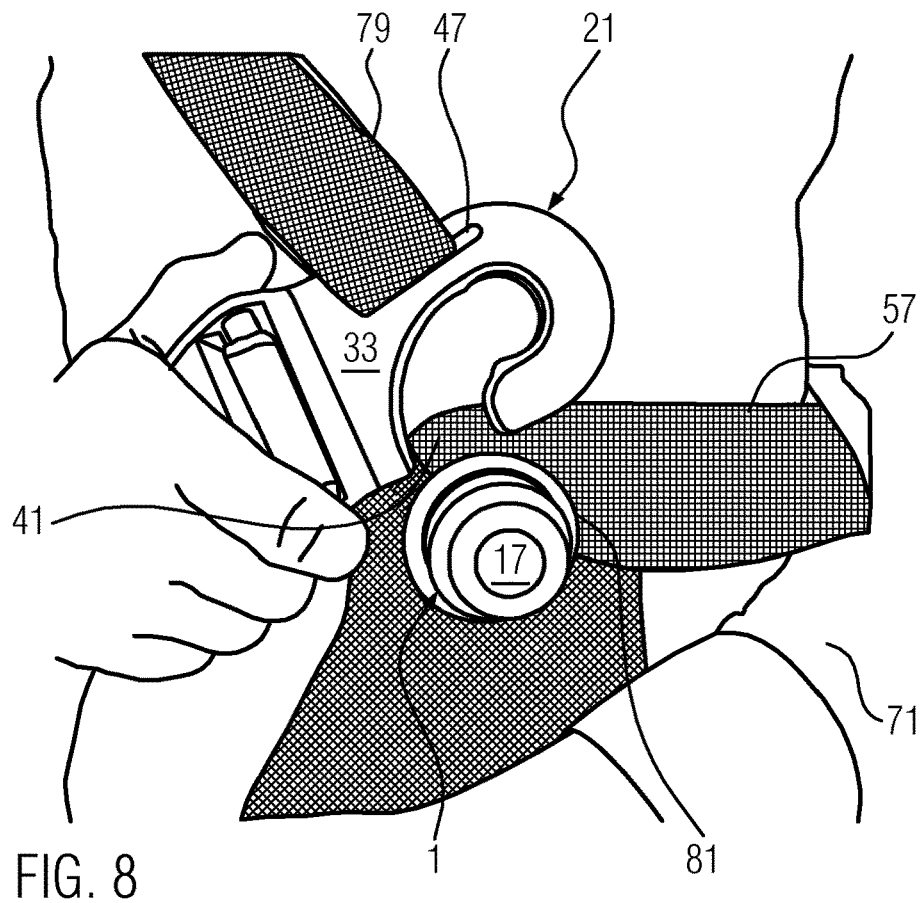
Figure 9:
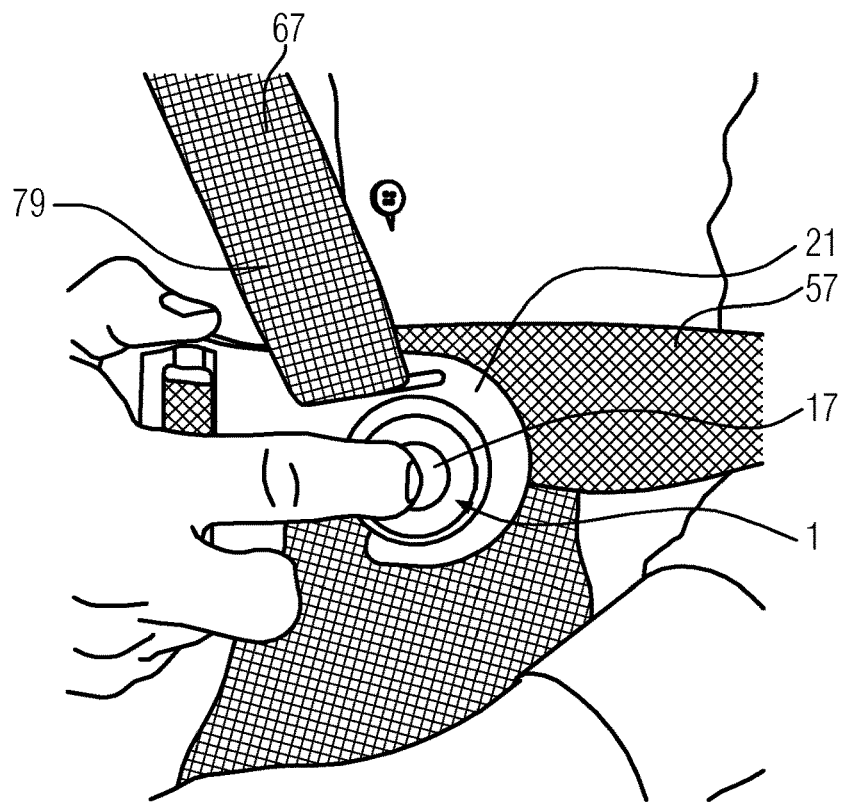
Figure 10:
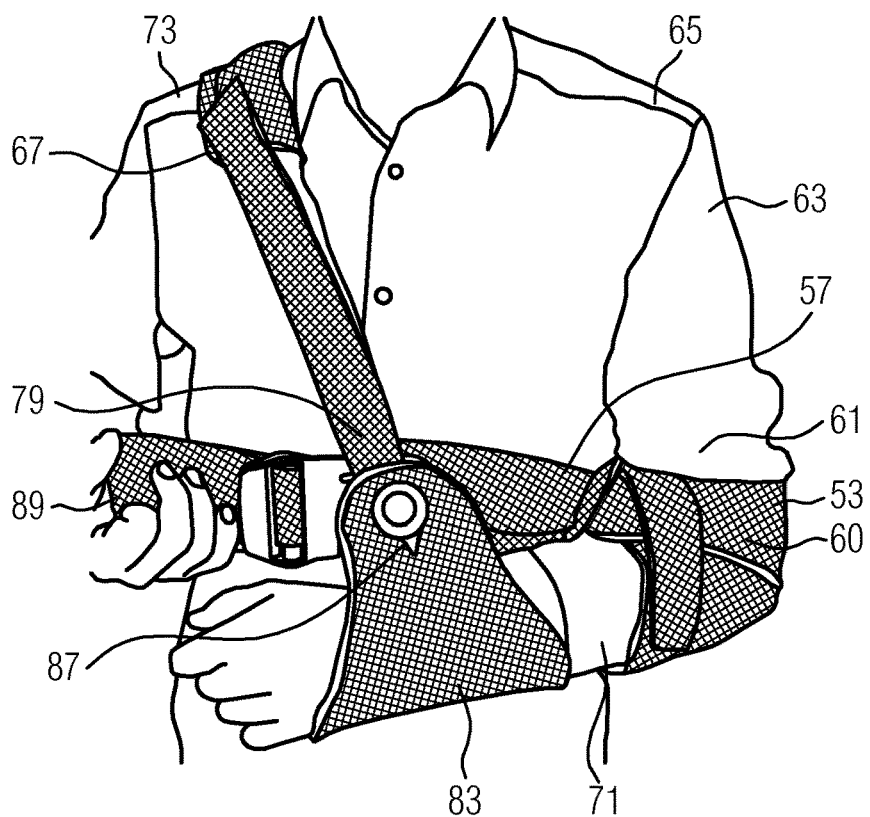
Figure 11:
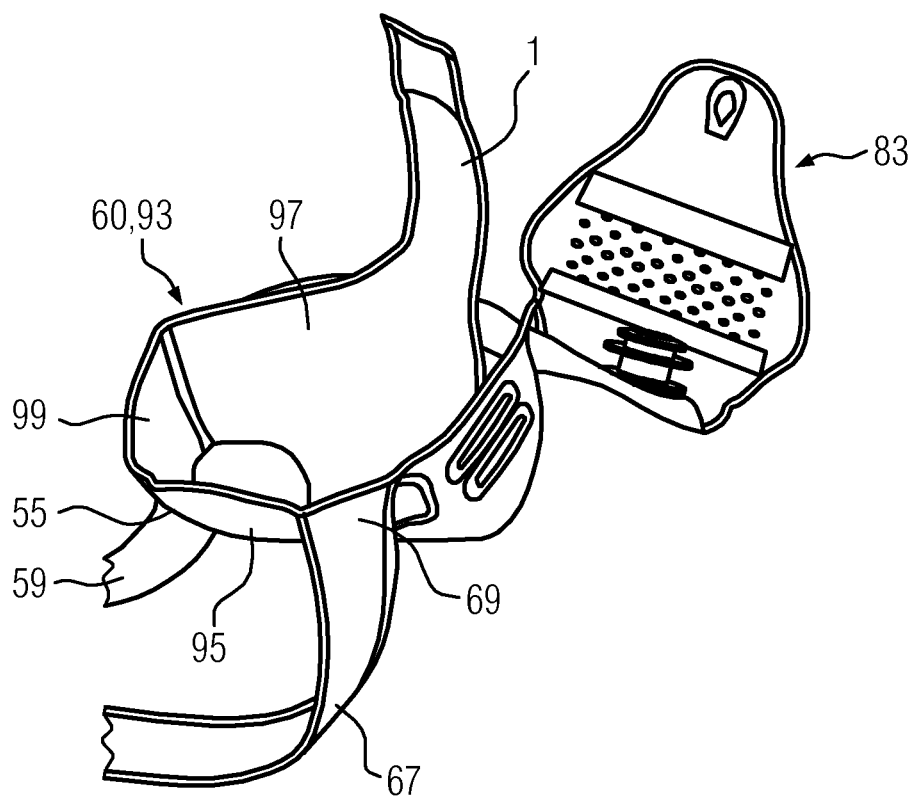
Figure 12:
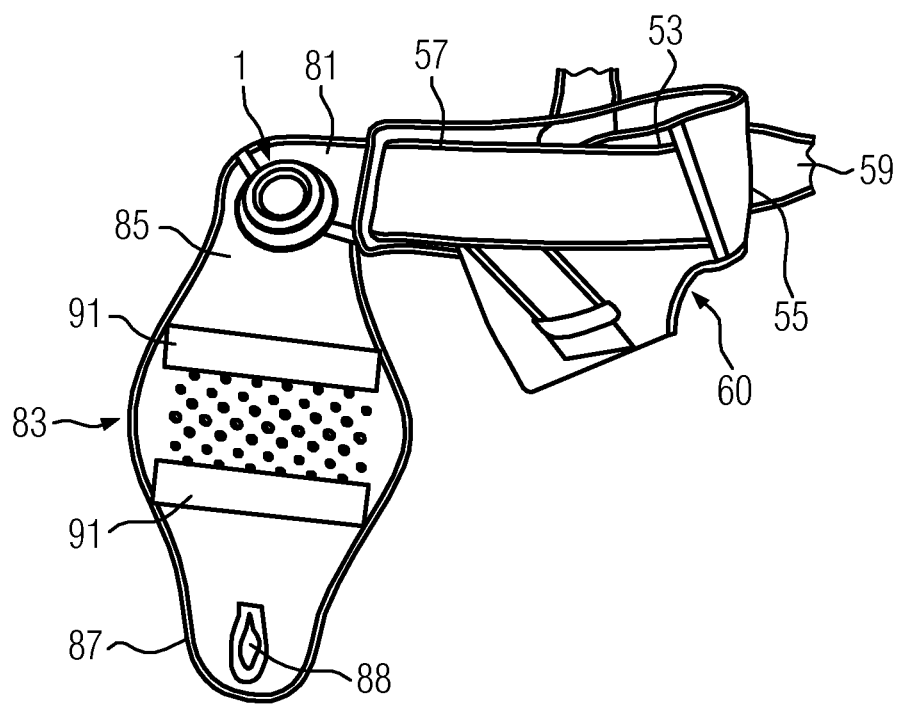
Figure 13:
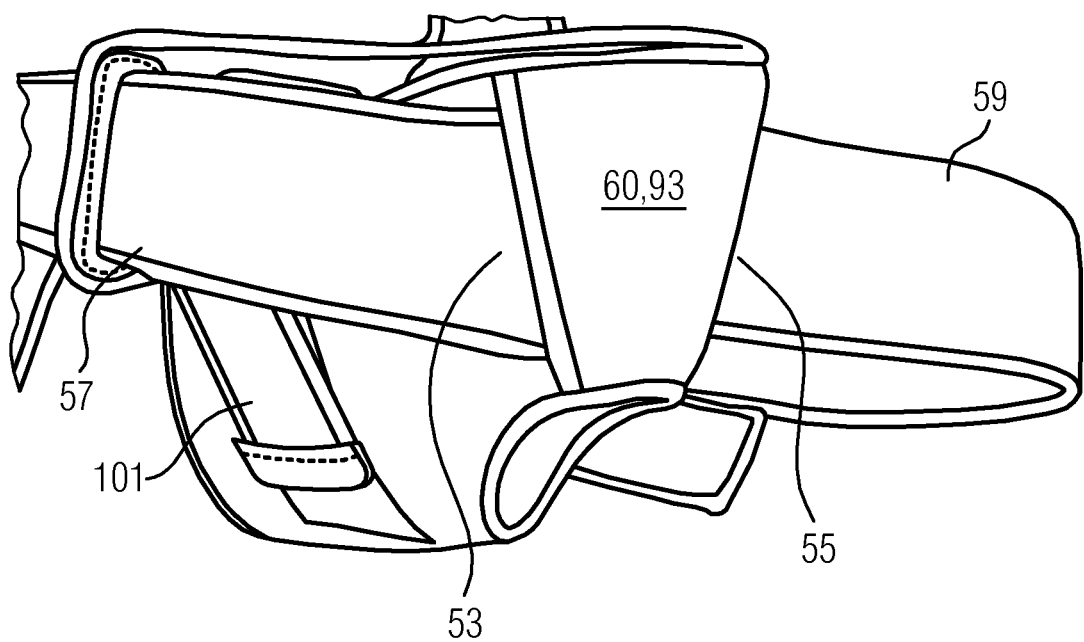

The present invention is explained below with reference to a drawing showing a preferred exemplary embodiment, in which FIG. 1 shows the first closure part of the exemplary embodiment in a perspective view, FIG. 2 shows the second closure part in a top view, FIG. 3 shows the first closure part in a side view, FIG. 4 shows a perspective representation of the exemplary embodiment of the closure in the closed state, FIG. 5 shows the front part of a shoulder orthosis having the exemplary embodiment of the closure, with the orthosis not being fully closed, FIG. 6 shows the rear part of the orthosis of FIG. 5, FIG. 7 shows the side part of the orthosis of FIGS. 5 and 6, FIG. 8 shows in detail the orthosis of FIG. 5 through 7 having the exemplary embodiment of the closure in the open position thereof, FIG. 9 shows in detail the orthosis of FIG. 5 through 7 having a closed closure, FIG. 10 shows the front part of the orthosis of FIG. 5 through 7 in a fully closed and fitted on state, FIG. 11 shows the elbow section of the orthosis of FIG. 5 through 7 in an open position, FIG. 12 shows the elbow section of the orthosis of FIG. 5 through 7 in a closed position and FIG. 13 shows the elbow section of the orthosis of FIG. 5 through 7 in a side view.

FIGS. 1 through 4 firstly show the exemplary embodiment of a closure according to the invention, without this closure being connected to the belt assembly of an orthosis.

The first closure part 1 of the exemplary embodiment shown in FIGS. 1 and 3 comprises a pin 3 and has a connecting means designed as a flange 5, by means of which it can be connected to an end of a belt of a belt assembly, for example by means of welding, bonding or sewing together. The pin 3 of the first closure part 1 is provided with a first section 7, which extends between a first projection 9 and a second section designed as a second projection 11. Thus the first section 7 is disposed near to the connecting means designed as a flange 5, and the second section or the second projection 11, respectively, connects, at the end of the first section 7 opposite the connecting means, or the flange 5, respectively, to said first section. The diameter and thus the dimensions of the projections 9, 11 perpendicular to the direction of extension of the pin 3 are larger than the diameter or the dimensions of the cylindrical first section 7.

On the side of the first section facing away from the flange 5, an undercut 13 is provided on the pin 3, which serves to receive a recess in a belt end. The undercut 13 on the free end of the pin 3 thus represents another connecting means, by means of which, for example, another belt can be detachably connected to the first closure part 1. As can finally be seen in FIG. 1, the free end 15 of the pin 3 facing away from the flange 5 has an indentation 17 extending in the axial direction of the pin 3, which is dimensioned such that it can receive the finger of a patient and the first connection part 1 can thus be held in position, when the closure is closed. In order to also securely hold the first closure part 1, a plurality of projections 19 are provided at the end surface of the free end 15 around the indentation 17, which also prevent any slipping of the patient's finger.

The second closure part 21 is shown in a top view in FIG. 2. The second closure part 21 has a connection end 23 and a coupling end 25.

A first connecting means for a belt end is provided in the region of the connection end 23, which, in this exemplary embodiment, is designed such that a first slot 29 and a second slot 31 extend parallel to a web 27, with the second slot 31 being further distanced from the connection end 23 than the first slot 29. In order to connect a belt end to the first connecting means, this belt end is guided out of the connection end 23 along a side of the second connection part 21 and firstly through the second slot 31, then around the web 27, and finally through the first slot 29 and back again to the connection end 23. Because the first slot 29 is delimited by a sharp edge on the side facing away from the web 27, a belt end can thus be connected in a self-fixing manner to the first connecting means, with the position of the belt end relative to the second connection part 21 being adjustable.

The second closure part 21 also has a flat section 33, which extends away from the connection end 23 or the first connecting means 27, 29, 31, respectively, to the coupling end 25. The flat section 33 thus extends along a connecting line 35 between the connection end 23 and the coupling end 25. A guide track 37 is designed as a recess in the flat section 33, which is surrounded by an abutment section formed by a web 39 with constant thickness, so that the flat section 33 in the region around the guide track 37 is designed with a uniform thickness. Thanks to the web 39, the thickness of the flat section 33 in the region of the guide track 37 corresponds to the distance between the first and second projections 9, 11 or the length of the first section 7 in the axial direction of the pin 3, respectively, so that the first closure part 1, when it is located in the guide track 37, cannot move in the axial direction of the pin 3 relative to the second closure part 21. In addition, the guide track 37 extends in a closure plane defined by the flat section 33.

The guide track 37 has a uniformly curved course and extends from an entrance opening 41 to a guide track end 43, with the entrance opening 41 being formed, in this preferred exemplary embodiment, at the edge of the flat section 33 and thus of the second closure part 21. The entrance opening 41 is designed, irrespective of its position in the second closure part 21, such that the first closure part 1 can be introduced through it into the guide track 37. If the entrance opening 41 is formed in the edge, the second closure part 21 can simply be moved onto the first section 9 of the pin 3. However, it is also conceivable that the entrance opening is realized as a bore having larger dimensions relative to the guide track end 43, so that the second section, or the second projection 11, respectively, can firstly be pushed through the bore, before the first section 7 is then moved in the guide track 37, with the edge of the guide track 37 then being in contact with the first section 7.

The guide track 37 is thus designed such that any possible movement 44 of the pin 3, with the position of its first section 7 in the guide track end 43 being indicated with dashed lines in FIG. 2, from its position in the guide track end 43 runs such that at least the projection of this movement 44 is directed on the connecting line 35 toward the connection end 23. In the exemplary embodiment shown here, the movement 44 of the pin 3 itself runs parallel to the connecting line 35.

However, it is also conceivable that the movement runs inclined to the connecting line. In any case, the guide track 37 is designed at the guide track end 43 such that the movement either has at least one component which is directed toward the connection end 23 or the movement runs perpendicular to the connecting line 35.

Thus the path of movement away from the guide track end 43 has no component which, on the one hand, runs parallel to the connecting line 35 and, on the other hand, is directed toward the coupling end 25. In other words, when the pin 3 is to be moved from the guide track end 43 to the entrance opening 41, it must be forcibly moved away from the coupling end 25. In order to realize such a movement, the first closure part 1 must, when the closure is integrated into a belt assembly of an orthosis, be moved against the force which is exerted by the preload of the belt assembly on the closure. This results in the closure self-locking. However, it is also conceivable that the movement of the pin 3 out of the guide track end 43 runs perpendicular to the connecting line 35 between the connection end 23 and the coupling end 25. Then, when the closure is under stress, at least frictional forces are applied, which prevent a movement of the pin 3 in the guide track 37.

As can additionally be seen from FIG. 2, the connecting line 35, apart from that, extends from the connection end 23 having the first connecting means, through the guide track end 43 to the coupling end 25, with the connecting line 35 also extending through the central axis of the pin 3 or of the first section 7, respectively, if this is located in the guide track end 43.

The width X of the guide track 37, and thus its dimensions perpendicular to the tangent on its course, corresponds to the diameter of the first section 7 of the first closure part 1 with the exception of a region between latching projections 45, in which the width is reduced. However, it is also conceivable that the width of the guide track 37 does not correspond to the dimensions of the first section 7 over its entire length, but is designed significantly larger at a distance to the guide track end 43. In any case, the dimensions of the second section or of the second projection 9, respectively, perpendicular to the direction of extension of the pin 3 must, however, be larger than the dimensions of the guide track 37 at the guide track end 43, so that the second section 9 delimits a movement of the pin 3 relative to the second closure part 21 perpendicular to the closure plane. The concept of the correspondence of the dimensions should be understood in this context to mean that the first section 7 and the edge of the guide track 37 in the guide track end 43 should not abut each other so tightly that a movement of the pin 3 relative to the second closure part 21 is no longer possible.

The latching projections 45 serve to lock the first closure part 1 in a position, in which it is situated at the guide track end 43. In this exemplary embodiment, the first closure part 1 together with the pin 3 must thus be moved past the projections 45, with these having to be moved out of and away from the guide track 37, counteracting an elastic counterforce produced by the elasticity of the flat section 33.

Because the pin 3 in the region of the first section 7 has a circular cross-section and corresponds to the diameter of the width x of the guide track, the first closure part 1 can be pivoted relative to the second closure part 21.

As can also be seen from FIG. 2, the guide track 37 is designed such that it can receive the first section 7 of the pin 3 and guide it between the entrance opening 41 and the guide track end 43. It can also be seen that the entrance opening 41, which is formed at the edge of the flat section 33, is designed such that its projection onto the connecting line 35 is further distanced from the coupling end 25 than the projection of the guide track end 43 onto the connecting line 35. Thus a force is also applied at the entrance opening 41 to the first closure part 1, when the closure is integrated into a belt assembly.

Finally, in the flat section 33 of the second connecting part, a second connecting means for a belt end is designed in the form of another slot 47, so that the second closure part 21 can be connected to a second belt end, which is guided through the other slot 47. The other slot 47 is on one side of the connecting line 35.

As can also be seen from FIG. 2, the entrance opening 41 of the guide track 37 is disposed on a first side of the connecting line 35, while the second connecting means in the form of the other slot 47 is disposed on an opposite second side.

When the closure parts 1, 21 of this exemplary embodiment are to be connected to one another and they are each connected to belt ends of a belt assembly, the second connecting part 21 must be moved, initially counteracting the return forces generated by the belt assembly, so far toward the first closure part 1 that the pin 3 can be moved laterally through the entrance opening 41 into the guide track 37 in the flat section 33. The pin 3 then moves, in this exemplary embodiment due to the uniform direction of curvature, along the guide track 37 and it must be moved past the projections 45, by means of pressing if necessary, until it reaches the guide track end 43. It is held in this position, since this is the point of the guide track 37 nearest to the coupling end 25, as a result of the return forces.

As can be seen from FIGS. 5 through 13, the exemplary embodiment of an orthosis, into which the previously described exemplary embodiment of a closure according to the invention can be integrated, is provided for the immobilization of a shoulder joint, and it has a belt assembly having a circular belt 51, which has a first and a second end 53, 55 (see FIGS. 5 and 6).

The circular belt 51 is composed of a front section 57 extending from the first end 53 and passing over the patient at the front and a rear section 59, which runs from the second end 55 around the patient at the rear and horizontally. In this exemplary embodiment, the first and the second ends 53, 55 of the circular belt 51 are connected to one another in such a way that they are attached at a seat 60 for the elbow adjacent to one another, as shown in particular in FIG. 13. In this exemplary embodiment, the first end 53 of the circular belt 51 forms, with the seat 60, a first belt section, which partially wraps around an arm section 61 of the patient's arm 63, which extends from the first shoulder joint 65 to be immobilized.

The term "arm section" is understood in the context of the present invention to mean the area of the arm 63 commencing from the injured first shoulder joint 65, which includes the elbow itself as well as the adjacent areas.

It is also apparent from FIGS. 5, 6 and 7 that a shoulder belt 67 is provided in this orthosis, the first end 69 of which forms a second belt section, with the first end 69 being connected to the seat 60 and thereby also wrapping around the arm section 61 of the patient's arm 63. The first end 69 passes into the seat 60 at the forearm 71 adjacent to the elbow. The shoulder belt 69 extends at the rear and diagonally over the back of the patient to the shoulder 73 contralateral to the first shoulder joint 65. As FIGS. 5 and 10 show, the shoulder belt 67 runs from the contralateral shoulder 73 in the vertical direction at the front relative to the circular belt 51 and is connected to the latter there in a first connecting point via the closure parts 1, 21.

As can also be understood from FIG. 5 through 13, the closure having the closure parts 1, 21 is disposed, in the closed state of the orthosis, in the region of a virtual point of intersection 75 (see FIG. 5).

The second closure part 21 is connected to the second end 79 of the shoulder belt 67 in such a way that the second end 79 can be pulled through the other slot 47 and the second closure part 21 can thus be moved along the shoulder belt 67. In order to move the second end 79 of the shoulder belt 67, a Velcro fastening must first be opened, and then the second end 79 can be pulled more or less far through the other slot 47.

The second closure part 21 is also connected to the rear section 59 of the circular belt 51, with the second closure part also being displaceable in the longitudinal direction thereof. For this purpose, the rear section 59 is guided, in the manner already described, through the first and second slots 29, 31 and around the web 27.

The second end 79 of the shoulder belt 67 and the circular belt 51, or its rear section 59, respectively, are thus connected to one another by means of the second closure part 21. Furthermore, because the second closure part 21 is displaceably mounted on the circular belt 51 and the shoulder belt 67, a first connecting point, at which the shoulder belt 67 and the circular belt 51 are connected to one another, is displaceable along the circular belt 51 and along the shoulder belt 67.

The first closure part 1 is attached to the free end 81 of the front section 57 in such a way that the flange 5 is sewed to the free end 81. However, it is also conceivable that the flange 5 is bonded or welded to the free end 81.

The first section 7 of the pin 3 can be inserted into the entrance opening 41 and moved along the guide track 37 to the guide track end 43, in order to close the closure formed by the closure parts 1, 21. It can be seen that, both in the closed and in the open position, the shoulder belt 67 and the rear section 59 are connected to one another.

FIGS. 5 and 13 also show that a retaining belt 83 is provided, the first end 85 of which is connected to the free end 81 of the front section 57. The second end 87 of the retaining belt 83 can be detachably connected to the first connecting part 1, in that a recess 88 is made in the second end 87 in the region of the undercut 13 and is thus attached to the free end 15 of the pin 3, so that the retaining belt 83 forms a loop, in which the wrist of the forearm 71, which commences at the first shoulder joint 65, can be received (see FIG. 10). As can also be seen from FIG. 13, reinforcement braces 91 extend on the retaining belt 83 perpendicular to its direction of extension, which prevent bending deformation of the retaining belt 83, so that a wrist received by the retaining belt 83 cannot flex.

The two slots 29, 31 provided at the connection end 23 of the second closure part 21 and the web 27 disposed between them provide a fixing device, to fix along the rear section 59 the position of the first connecting point, at which the shoulder belt 67 and the rear section 59 are connected to one another. This fixing device is, in the construction described previously, designed in such a way that the first connecting point can, by pulling on the rear section end 89 spaced from the second end 55 of the circular belt 51, or of the rear section 59, respectively, be moved to the second end 55, while a movement of the first connecting point to the rear section end 89 is blocked by pulling on the second end 55. This means that the rear section 59 can be pulled, by pulling on its end 89 through the slots 29, 31, through the connection end 23, while a movement of the rear section 59 in the opposite direction is blocked.

As can finally be seen from FIGS. 11 through 13, the seat 60 for the elbow has an assembly allowing its width to be adjusted. The seat for the elbow has a main body 93, which comprises an inner surface 95 abutting the patient's body, an outer surface 97 disposed away from the body, and a lateral surface 99 abutting the outside of the upper arm. The inner surface 95 and the outer surface 97 are connected to one another at an edge, which abuts the forearm. An adjustment belt 101 is attached to the outer surface 97, on the edge lying spaced from the connection to the inner surface 95, which can be guided through two openings 103 in the inner surface and over the forearm, and which can, in turn, be detachably attached to the outer surface 97. By means of the adjustment belt 101, it is possible to adjust the width of the seat 60 to the patient's requirements.

The previously described exemplary embodiment of an orthosis is now fitted on as follows.

Firstly, the arm section 61 is received in the seat 60 connected to the ends 53, 69 of the circular belt 51 and of the shoulder belt 67, so that these then wrap around the arm section 61 via the seat 60. The adjustment belt 101 is guided over the forearm of the patient.

Because the second end 79 of the shoulder belt 67 and the rear section 59 are connected to one another via the second closure part 21, even in the open position of the closure, the rear section 59 and the shoulder belt 67 initially form a loop in which the shoulder 73 contralateral to the first shoulder joint 65 can be received, or the patient must simply hang this loop over the contralateral shoulder 73, respectively.

The closure formed by the closure parts 1, 21 is then closed in such a way that the pin 3 is inserted into the entrance opening 41 and is then pulled, as a result of the forces acting on the free end 81 of the front section 57, to the guide track end 43, wherein, however, they must be pushed out of the guide track 37, against the counterforces acting against them by the latching projections 45. FIG. 9, in particular, shows that the indentation 17 in the free end 15 of the pin 3 permits a closure of the closure with a movement of the pin 3 along the guide track 37 using just one hand.

If the pin 3 is located at the guide track end 43, it is held at the guide track end 43 as a result of the described course of the guide track 37 and of the force applied along the connecting line, which is generated by the preload in the circular belt 51 and the shoulder belt 67.

Finally, the circular belt 51 can then also be tightened by pulling on the rear section end 89, with the second closure part 21 being designed in the previously described manner, so that a backward movement of the rear section 59 is not possible. This then produces the situation shown in FIG. 5.

Finally, the patient can secure the forearm 71 in such a way that the retaining belt 83 is wrapped around the forearm, with the second end 87 of the retaining belt 83 being attached to the pin 3 of the first closure part 1 (see FIG. 10).

In the case of the previously described orthosis, a first and a second belt section, namely the first end 53 of the circular belt 51 and the first end 69 of the shoulder belt 67, are therefore provided, which are applied to the arm section 61 in such a way that they at least partially wrap around it with the help of the seat 60, so that, by pulling in the direction of extension of the belt sections, the arm section 61 is subjected to a first and a second force. The first belt section, or the first end 53 of the circular belt 51, respectively, applies a force (F1; see FIG. 5), in the fitted on state of the orthosis, in which the arm 63, commencing at the injured shoulder joint 65, abuts the body, laterally or frontally, to the arm section 61, which is directed toward the body and which preferably extends essentially parallel to the frontal plane of the patient, but which has at least a first component, which runs horizontal and parallel to the frontal plane. The arm section 61 is thus pulled toward the body as a result of the first belt section, so that the first force component acts on the first arm 63 in an adducent manner. At the same time, the second belt section, i.e. the first end 69 of the shoulder belt 67 applies a second force (F2; see FIG. 7) to the arm section 61, which has at least one component, which runs horizontal and parallel to the sagittal plane and thus perpendicular to the first component and is directed toward the rear, so that a slight retroversion of the arm 63 is effected. Thanks to this combination of the two force components, the arm 63 is reliably secured on the body.

A further advantage is that the first shoulder joint 65 to be immobilized is immobilized with both an extended elbow and with a bent elbow.

It is also apparent that the closure according to the invention, composed of the two closure parts 1, 21 described at the outset, provides the patient with the great advantage that, simply by release thereof, in other words, switching from the closed to the open position, the effect of both forces F1, F2 on the arm section 61 is removed, so that the arm 63, commencing at the injured shoulder joint 65, is immediately freed. Conversely, through simply closing the closure 1, 21, the effect of both forces F1, F2 can be immediately obtained, without additional measures being required on the part of the patient. This makes the fitting on process significantly easier.

In a general way, the previously described orthosis thus comprises a circular belt assembly 51, 57, 59, which is designed to pass around a patient in a circular and horizontal manner, and which has a first and a second section in the form of the rear section and the front section 57, 59, which are designed to be detachably connected at a point of intersection 75. This orthosis also includes a shoulder belt assembly 67, which has a first end 69 connected to the circular belt assembly 51, 57, 59 and a second end, and which is adjusted so as to pass from the rear to the front over a shoulder of the patient to the point of intersection 75. At the point of intersection 75, the first section of the circular belt assembly 51, 57, 59, namely the front section 57, is connected to the connecting means of the first closure part 1, while the second section, namely the rear section 59, is connected to the connecting means 27, 29, 31 of the second closure part 21. Finally, the shoulder belt assembly 67 is connected to the other connecting means 47 of the second closure part 21.

The design of the closure parts 1, 21 ensures that the closure can be closed easily, if necessary, with only one hand, and it maintains itself in this position, simply as a result of the course of the guide track 37. An orthosis equipped with the closure according to the invention can thus be fitted on and closed even by a patient having limited freedom of movement.

The invention claimed is:

1. A belt assembly closure for an orthosis comprising:
 (a) a first closure part having a pin and a first closure part connecting means adapted to connect to a belt of a belt assembly;

(b) a second closure part having:
   (i) a coupling end, an opposing connection end, and a connecting line between the coupling end and the connection end,
   (ii) a second closure part connecting means positioned on the connection end of the second closure part adapted to connect to another belt of the belt assembly,
   (iii) an arcuate guide track positioned between the coupling end and the connection end and extending in a closure plane from an entrance opening to a guide track end and adapted to receive and guide the pin between the entrance opening and the guide track end along the guide track by movement perpendicular to the connecting line for a releasable connection between the first closure part and the second closure part,
   (iv) the guide track entrance opening positioned between the connection end and the coupling end and formed on an edge of a first side of the second closure part, and
   (v) another second closure part connecting means positioned on a second side of the connecting line opposing the first side adapted for another belt of the belt assembly;
(c) the pin having a first section proximate to the first closure part connecting means and a second section adjoining the first section and positioned on an end of the first section opposite the first closure part connecting means; and
(d) wherein dimensions of the first section of the pin perpendicular to the direction of extension of the pin correspond to the dimensions of the guide track in the closure plane at the guide track end, and dimensions of the second section of the pin perpendicular to the direction of extension of the pin are greater than the dimensions of the guide track at the guide track end so that the second section restricts movement of the pin relative to the second closure part perpendicular to the closure plane.

2. The closure according to claim 1, wherein the guide track end and the pin are designed such that the first closure part is pivotable relative to the second closure part, when the pin is located on the guide track end.

3. The closure according to one of claim 1, wherein locking means are provided in order to hold the pin in the guide track.

4. The closure according to claim 3, wherein a latching projection is formed in the guide track, so that guide track width is reduced in a region of the latching projection, and
   wherein the second closure part is designed such that, the first section of the pin, when moving from the entrance opening to the guide track end and back again, must be moved past the latching projection, against an elastic counterforce.

5. The closure according to one of claim 1, wherein an abutment section with uniform thickness is provided adjacent to the guide track in a region of the guide track end, and
   wherein the first section of the pin has, in an axial direction, a length corresponding to the thickness of the abutment section.

6. The closure according to claim 1, wherein the entrance opening is further spaced from the coupling end than of the guide track end.

7. The closure according to claim 1, wherein the guide track extends with a uniform direction of curvature from the entrance opening to the guide track end.

8. The closure according to claim 7, wherein the guide track is designed at the guide track end such that the movement of the pin out of the position on the guide track end runs parallel to the connecting line between the connection end and the coupling end.

9. The closure according to one of claim 1, wherein the first closure part is designed such that the pin extends away from the connecting means and has a free end and wherein the free end has an indentation extending in the axial direction of the pin.

10. The closure according to one of claim 1, wherein an abutment section with uniform thickness is provided adjacent to the entire guide track, and
    wherein the first section of the pin has, in an axial direction, a length corresponding to the thickness of the abutment section.

11. The closure according to one of claim 1, wherein locking means are provided in order to hold the pin in the guide track at the guide track end.

12. A belt assembly closure for an orthosis comprising:
(a) a first closure part having a pin and a first closure part connecting means adapted to connect to a belt of a belt assembly;
(b) a second closure part having:
   (i) a coupling end, an opposing connection end, and a connecting line between the coupling end and the connection end,
   (ii) a second closure part connecting means positioned on the connection end of the second closure part adapted to connect to another belt of the belt assembly,
   (iii) an arcuate guide track positioned between the coupling end and the connection end and extending in a closure plane from an entrance opening to a guide track end and adapted to receive and guide the pin between the entrance opening and the guide track end along the guide track by movement perpendicular to the connecting line, and to guide and release the pin by movement having a projection directed onto the connecting line which moves toward the connection end for a releasable connection between the first closure part and the second closure part,
   (iv) the guide track entrance opening positioned between the connection end and the coupling end and formed on an edge of a first side of the second closure part, and
   (v) another second closure part connecting means positioned on a second side of the connecting line opposing the first side adapted for another belt of the belt assembly;
(c) the pin having a first section proximate to the first closure part connecting means and a second section adjoining the first section and positioned on an end of the first section opposite the first closure part connecting means; and
(d) wherein dimensions of the first section of the pin perpendicular to the direction of extension of the pin correspond to the dimensions of the guide track in the closure plane at the guide track end, and dimensions of the second section of the pin perpendicular to the direction of extension of the pin are greater than the dimensions of the guide track at the guide track end so that the second section restricts movement of the pin relative to the second closure part perpendicular to the closure plane.

* * * * *